United States Patent [19]

Sekine

[11] Patent Number: 5,349,399
[45] Date of Patent: Sep. 20, 1994

[54] INTRAOCULAR LENGTH MEASURING INSTRUMENT HAVING PHASE COMPENSATING MEANS

[75] Inventor: Akihiko Sekine, Tokyo, Japan

[73] Assignee: Kabushiki Kaisha Topcon, Tokyo, Japan

[21] Appl. No.: 41,997

[22] Filed: Apr. 2, 1993

[30] Foreign Application Priority Data

Apr. 3, 1992 [JP] Japan .................................. 4-081981

[51] Int. Cl.$^5$ .............................................. A61B 3/10
[52] U.S. Cl. .................................... 351/215; 351/211; 351/221
[58] Field of Search ............... 351/215, 211, 221, 232, 351/205; 356/357, 358, 309; 395/494, 499

[56] References Cited

U.S. PATENT DOCUMENTS

| | | | |
|---|---|---|---|
| 4,153,335 | 5/1979 | Buchan | 356/390 |
| 4,636,088 | 1/1987 | Rosencwaig et al. | 356/357 |
| 5,141,302 | 8/1992 | Arai et al. | 351/221 |

Primary Examiner—William L. Sikes
Assistant Examiner—Hung Xuan Dang
Attorney, Agent, or Firm—Finnegan, Henderson Farabow, Garrett & Dunner

[57] ABSTRACT

To obviate the influence of, for example, birefringence of an eyeball, an intraocular length measuring instrument includes a light source portion for emitting a measuring beam of linearly polarized light; a beam splitter for separating a beam of light reflected by an intraocular object to be measured from the measuring beam of light projected from the light source portion onto the intraocular object; a light receiving portion for receiving the reflected beam of light separated by the beam splitter; and a phase compensating means disposed between the eye to be measured and the beam splitter, for transforming the beam reflected from the intraocular object into a beam of light with a polarization component substantially perpendicular to the measuring beam of linearly polarized light emitted from the light source portion.

3 Claims, 8 Drawing Sheets

INTRAOCULAR LENGTH MEASURING INSTRUMENT HAVING PHASE COMPENSATING MEANS

BACKGROUND OF THE INVENTION

1. Field of the Invention

This invention relates to an instrument for measuring the length of an intraocular length, such as an axis of a subject's eye by projecting a measuring beam of light onto the eye.

2. Description of the Prior Art

A conventional instrument in the art is known in which a position of the cornea of the eye with respect to the instrument is obtained by the aid of geometrical optics, a position of the eye fundus with respect thereto is obtained by the aid of physical optics, and an eye axis length is measured from a difference between the two positions without contact of the instrument with the eye.

This conventional instrument first projects a measuring beam of linearly polarized light emitted from a light source, such as a laser diode, onto the eye fundus and a reference surface. Interference is then made between light beams reflected from the eye fundus and the reference surface. After that, the resultant interference light is received by a light receiving element and causes interference fringes to occur on the light receiving surface of the element. An output signal from the element is then processed by an arithmetic circuit to determine the position of the eye fundus with respect to the instrument.

If noises, such as those due to abnormal refraction, do not occur in an optical path between the instrument and the eye fundus, the two reflected light rays can be caused to interfere with each other without giving any optical treatment to the rays. The position of the eye fundus determined as described above is thus satisfactory in accuracy.

However, there are some cases where the eye ball of the subject's eye has abnormal refraction (birefringence). In that case. linearly polarized light projected onto the eye becomes two rays of polarized light, i.e., an ordinary ray and an extraordinary ray, when the projected light is reflected from the eye fundus. These two rays have a phase difference.

The intensity of the interference light on the light receiving surface in a case where interference is made between the light rays reflected from the eye fundus and the reference surface having a phase difference is far less than that in a case where interference is made between the light rays having no phase difference. (The light ray reflected from the eye fundus is a measuring light ray.) That is, if light rays reflected from the eye fundus and the reference surface having a phase difference are caused to interfere with each other, an output signal from the light receiving element becomes unclear, in other words, the contrast between interference fringes produced on the light receiving surface decreases. Therefore, measurement of the eye axis length is inaccurate.

SUMMARY OF THE INVENTION

It is therefore an object of the invention to provide an intraocular length measuring instrument capable of decreasing the influence of birefringence of an eye ball.

To accomplish the object, an intraocular length measuring instrument according to a first embodiment of the invention comprises a light source portion for emitting a measuring beam of linearly polarized light and a beam splitter for separating a ray of light reflected by an intraocular object of the eye to be measured from the measuring beam of light projected from the light source portion onto the intraocular object. A light receiving portion is provided for receiving the reflected ray separated by the beam splitter. Phase compensating means, disposed between the eye to be measured and the beam splitter, causes the reflected light from the intraocular object to become a ray of light having a polarization component perpendicular to the measuring beam of linearly polarized light emitted from the light source portion.

To accomplish the object, an intraocular length measuring instrument according to a second embodiment of the invention comprises a light source portion for emitting a measuring beam of light and a measuring optical system for projecting the measuring beam of light onto an intraocular object of the eye to be measured. A beam splitter is provided for separating a part of the measuring beam from the measuring beam, and a reference optical system is provided for guiding the separated part of light to a reference mirror. An interference optical system makes interference between light reflected from the eye fundus of the eye and light reflected from the reference mirror. A light receiving portion receives interference light produced by the interference optical system. Phase compensating means disposed, between the eye to be measured and the beam splitter, causes light reflected from the intraocular object to have a given phase difference with respect to the measuring beam of light projected onto the intraocular object. Preferably, the phase compensating means is a Babinet compensator.

Since these first and second invention embodiments are designed so that the phase compensating means compensates the birefringence of the subject's eye, an intraocular length (for example, an eye axis length) can be measured without the influence of the birefringence.

DETAILED DESCRIPTION OF THE EMBODIMENT

An intraocular length measuring instrument according to the invention will be hereinafter described with reference to the appended drawings.

Figure 1:
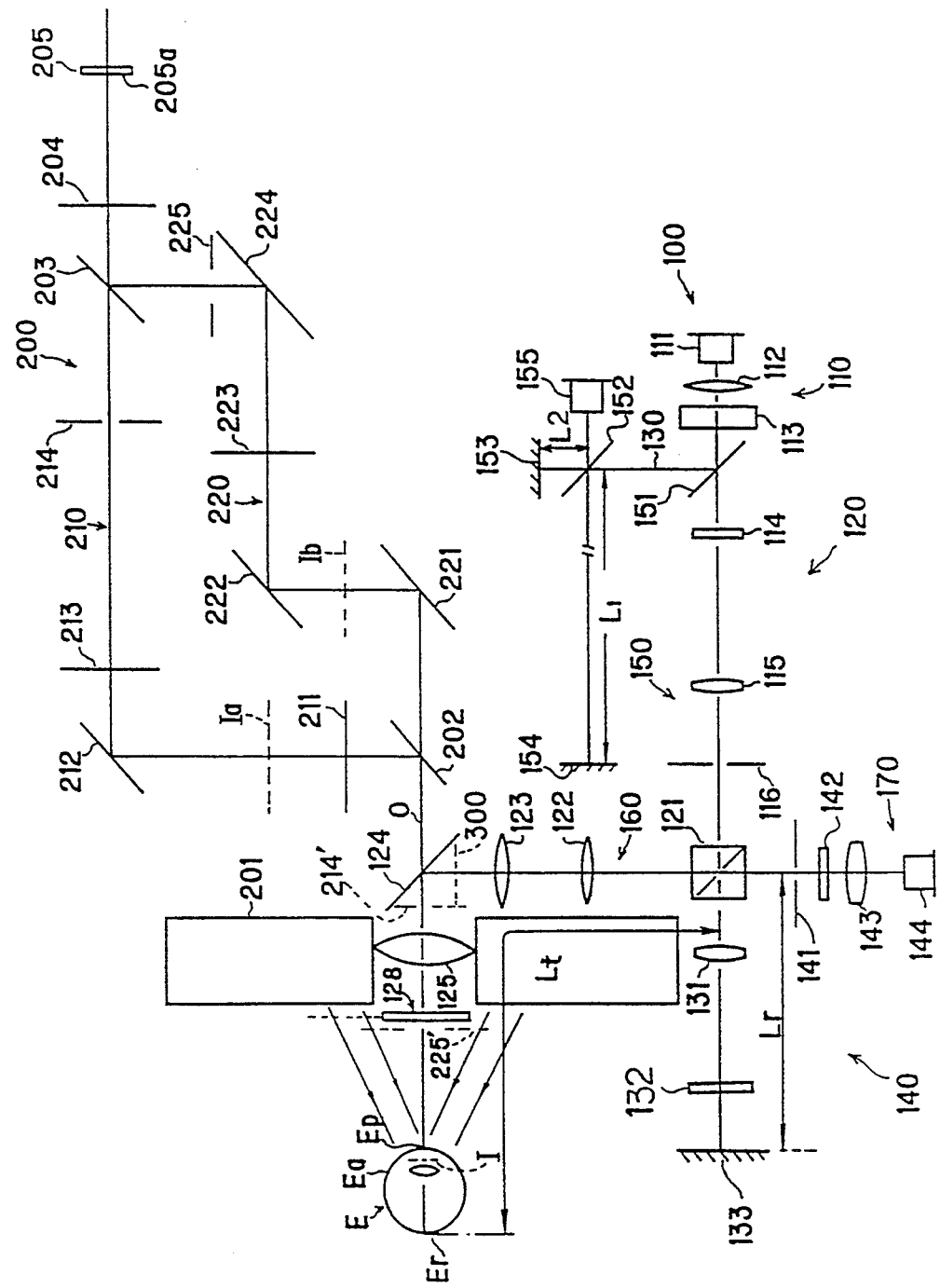
FIG. 1 is a view showing an optical system of an intraocular length measuring instrument according to the invention.

Referring first to FIG. 1, the numerals 100 and 200 denote an eye fundus distance measuring optical system and a cornea distance measuring optical system, respectively.

The eye fundus distance measuring optical system 100 includes a laser beam emitting optical system 110, an eye fundus reflection light measuring optical system 120 for obtaining an interference signal for finding a position of the eye fundus by means of a laser beam, and a base interference optical system 130 for obtaining a base interference signal by means of the laser beam. The laser beam emitting optical system 110 includes a semiconductor laser 111, a collimator lens 112 for transforming the laser beam into a beam of parallel rays, and an optical isolator 113 for preventing a reflected laser beam from entering the semiconductor laser 111.

The semiconductor laser 111 is provided with a heating and cooling plate (not shown). The heating and cooling plate is provided with a Peltier effect type of element (not shown). The control of the Peltier effect type of element leads to the control of the temperature of a chip of the semiconductor laser 111 and results in all operational stability of the laser 111.

The eye fundus reflection light measuring optical system 120 includes a measuring light projecting optical system (measuring optical system) for projecting a beam emitted from the laser beam emitting optical system 110 onto the eye fundus Er of the eye E, and a reference optical system 140. The measuring light projecting optical system (measuring optical system) includes a measuring light emitting optical system 150, a beam splitter 121, and a measuring light guiding optical system 160.

The eye fundus reflection light measuring optical system 120 includes a measuring light interference optical system (interference optical system) for making interference between light reflected from the eye fundus Er and reference light. The measuring light interference optical system includes the beam splitter 121 and a light receiving optical system 170.

The optical systems 140, 150, 160, and 170 are each arranged as follows.

The reference optical system 140 includes a collimator lens 131 which one of two beams of light split by the beam splitter 121 enters, a quarter wavelength plate 132, and a reference mirror 133.

The measuring light emitting optical system 150 includes a polarizer 114 for transforming the laser beam emitted from the laser beam emitting optical system 110 into a beam of linearly polarized light, a condenser lens 115, and a spatial filter 116. The polarizer 114, the semiconductor laser 111 and so on make up a light source portion for emitting a measuring beam of linearly polarized light.

The measuring light guiding optical system 160 includes the beam splitter 121, a collimator lens 122, a refraction compensating lens 123, a dichroic mirror 124, an objective lens 125, and a Babinet compensator (phase compensating means) 128. The dichroic mirror 124 serves to reflect a beam of wavelengths belonging to the laser beam and transmit a beam of the other wavelengths.

For convenience of illustration, let us suppose that the Babinet compensator 128 is designed so as to produce a phase difference of a quarter wavelength. In this case, the Babinet compensator 128 serves as a quarter wavelength plate to transform the beam of linearly polarized light incident upon the Babinet compensator 128 into a beam of circularly polarized light. A detailed description of the arrangement and function of the Babinet compensator 128 will be given hereinafter.

The light receiving optical system 170 includes a diaphragm 141, an analyzer 142 for transmitting a component of polarized light perpendicular to a beam of polarized light transmitted through the polarizer 114, an image forming lens 143, and a light receiver 144.

The base interference optical system 130 includes a beam splitter 152 for splitting one of the two beams split by the beam splitter 151 into two beams of light, total reflection mirrors 153, 154, and a light receiver 155 for receiving interference light made by beams of light reflected from the total reflection mirrors 153, 154. A base optical path difference (L1–L2), i.e. an optical path difference between the distance from the beam splitter 152 to the total reflection mirror 153 and the distance from the beam splitter 152 to the total reflection mirror 154, is arranged much longer than an eye axis length $L_{eye}$.

The cornea distance measuring optical system 200 includes a ring light illuminating optical system 201, a first imaging optical system 210, and a second imaging optical system 220. The first imaging optical system 210 includes an objective lens 125, a half mirror 202, a relay lens 211, and a two-dimensional imaging element 205. The second imaging optical system 220 includes the objective lens 125, mirrors 221, 222, a relay lens 223, a mirror 224, a diaphragm 225, a half mirror 203, an image forming lens 204, and the two-dimensional imaging element 205.

The laser beam emitted from the semiconductor laser 111 comes to the beam splitter 151 via the collimator lens 112 and the optical isolator 113. This laser beam is split into two beams by the beam splitter 151. One of the split beams is transformed into a beam of linearly polarized light by the polarizer 114. This beam of linearly polarized light comes to the beam splitter 121 via the condenser lens 115 and the spatial filter 116.

The beam splitter 121 splits the beam incident thereon into two beams. One of the split beams is condensed to the eye fundus Er as a beam of circularly polarized light via the collimator lens 122, the refraction compensating lens 123, the dichroic mirror 124, the objective lens 125, and the Babinet compensator 128. A beam reflected from the eye fundus Er is transformed into a beam of linearly polarized light by the Babinet compensator 128 and comes to the beam splitter 121 via the objective lens 125, the dichroic mirror 124, the refraction compensating lens 123, and the collimator lens 122. The other one of the two beams split by the beam splitter 121 comes to the reference mirror 133 as a beam of circularly polarized light via the collimator lens 131 and the quarter wavelength plate 132 and is reflected therefrom. This reflected beam of light is transformed into a beam of linearly polarized light by the quarter wavelength plate 132 and comes to the beam splitter 121 via the collimator lens 131. This beam of linearly polarized light has a polarization direction perpendicular to that of light polarized by the polarizer 114. These reflected beams from the eye fundus and the reference mirror 133 are synthesized by the beam splitter 121. Its resultant interference light enters the light receiving optical system 170.

This interference light is condensed to the diaphragm 141 by the collimator lenses 122, 131. The diaphragm 141 obviates and beams except the beams of light reflected from the eye fundus Er and the reference mirror 133. The interference light transmitted through the diaphragm 141 comes to the analyzer 142. The analyzer 142 transmits only light having a polarization component perpendicular to the polarized light transmitted through the polarizer 114. Therefore, only the interference light is received by the light receiver 144, while the other unfavorable light is obviated. The interference light received by the light receiver 144 has twice as much optical path difference as the difference between an optical path Lt from the beam splitter 121 to the eye fundus Er and an optical path Lr from the beam splitter 121 to the reference mirror 133.

If signals output by the light receivers 144, 155 when the wavelength of the beam emitted by the laser 111 is changed within a given range are processed in such a manner as described hereinafter, an optical path (Lt-Lr) from a base surface 300 to the eye fundus can be obtained. A description of the processing manner will be now given hereinafter.

An optical path difference between the double way of the optical path from the beam splitter 121 to the eye fundus Er of the interference optical system 120 and the double way of the optical path from the beam splitter 121 to the reference mirror (reference surface) 138 of the reference optical system 140 is twice as much as the optical path length (Lt-Lr) between the base surface 300 formed by the reference surface 133 and the eye fundus Er.

An initial phase difference at the light receiver 155 is $2\pi(L/\lambda)$ and a phase difference obtained after varying a wavelength of the laser beam is $2\pi\{L/(\lambda+\Delta\lambda)\}$ where L (constant) is an optical path difference of the base optical path of the base interference optical system 130 and equals $2(L1-L2)$, $\lambda$ is a wavelength of the laser beam, and $\Delta\lambda$ is the amount of variation of the wavelength. When the wavelength is continuously varied, the phase difference is consecutively varied from $2\pi(L/\lambda)$ to $2\pi\{L/(\lambda+\Delta\lambda)\}$. On the supposition of $\lambda>>\Delta\lambda$, the phase difference obtained after the wavelength is varied is $2\pi(L/\lambda-L\Delta\lambda/\lambda^2)$. The amount of variation of the phase difference is $2\pi(L\Delta\lambda/\lambda^2)$. In response to the variation of the wavelength, the intensity of interference fringes observed at the light receiver 155 is periodically varied.

Also, the amount of variation of the phase difference is $2\pi\{2(Lt-Lr)\Delta\lambda/\lambda^2\}$ at the light receiver 144 and the intensity of interference fringes observed thereat is periodically varied. The optical path length (Lt-Lr) is calculated from an intensity signal of the interference fringes varied periodically.

The following equations are therefore obtained.

$$\phi1=2\pi\{2(Lt-Lr)\Delta\lambda/\lambda^2\} \quad (A)$$

$$\phi2=2\pi(L\Delta\lambda/\lambda^2) \quad (B)$$

where $\phi1$ is the amount of variation of the phase difference at light receiver 144 and $\phi2$ is the amount of variation of the phase difference at the light receiver 155.

By eliminating $\Delta\lambda/\lambda^2$ from the equations (A) and (B), they are transformed as follows:

$$Lt-Lr=L\cdot\phi1/\phi2 \quad (C)$$

Accordingly, the optical path length (Lt-Lr) is measured from the amount of variation of the phase difference between the signals obtained at the light receivers 144, 155.

Descriptions of wavelength variation and signal processing will be now given hereinafter.

Figure 3:
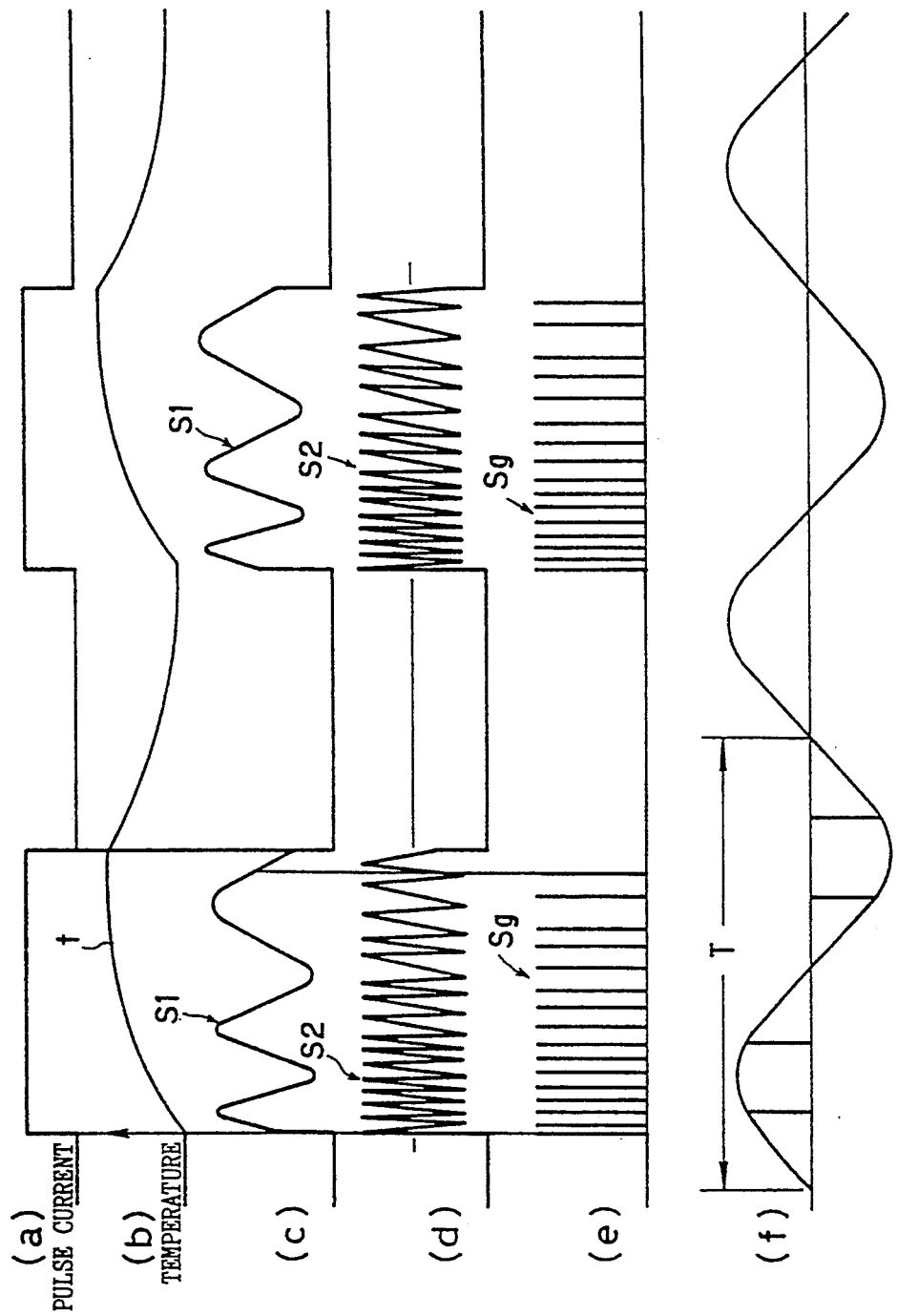
FIG. 3 is an illustration showing a waveform etc., output from each circuit of the control system of FIG. 2.

The semiconductor laser 111 is driven like a pulse (see (a) of FIG. 3). When the laser 111 is turned on, the temperature of the chip of the laser 111 starts rising. A given time is required until its temperature balance. An oscillation wavelength of the laser beam is varied in response to the variation of the temperature of the chip of the laser 111. The relationship of the temperature and the wavelength is in the ratio of 1:1 except a point where a mode hop (mode jump) occurs. That is, when the laser 111 is turned on, the chip temperature starts varying. Incidentally to this variation, the wavelength of the beam emitted from the laser 111 begins to be varied.

As shown in (b) of FIG. 3, the variation of the temperature is abrupt immediately after the laser 111 begins to be driven and it gradually calms down. After a lapse of a given time, the laser 111 is turned off to return the temperature to the former condition and stops emitting the beam. If a width of the pulse is properly arranged, reproductivity of the variation of the wavelength can be obtained. For example, if the laser 111 is rectangularly driven at the speed of 1 KHz or so, a principal part of the wavelength variation in response to the temperature variation is available. Further, the reproductivity of the wavelength variation can be accomplished.

The semiconductor laser 111 is used in which an interval of distance of mode hops is broader than a width of the wavelength variation. A base temperature, i.e., base wavelength of the laser 111 is controlled by a Peltier element (not shown) via a drive controlling circuit 301 shown in FIG. 2 in order to prevent the mode hop from occurring during the temperature variation for a pulse duration.

Since the variation of an oscillation output calms down much more quickly than the temperature variation, the intensity variation for the pulse duration will hardly occur. There is a transition duration until the output becomes stabilized after a rectangular input is applied and the laser 111 is turned on. (The output variation corresponding to the transition duration is not shown in (a) of FIG. 3.) Therefore, in practice, the laser beam is employed after the point of time at which the transition duration finishes. However, the wavelength variation for the duration that time is not linear but so curved as to have an abrupt rise in the initial stage of the duration and decrease gradually, and therefore the frequency of the signal to be obtained is high in the initial stage and becomes low little by little.

As shown in (c) and (d) of FIG. 3, the frequencies of signals S1 and S2 output from the light receivers 144 and 155 respectively are also high in the initial stage and becomes low gradually with the lapse of time. If the signals S1 and S2 are converted without giving any treatment to them from analogue to digital by an A/D converter 304 and a trigger with a constant frequency and its resultant data are used in that condition, the frequencies of the signals to be recorded are high in the initial stage of the duration and become low gradually. Therefore, each period of the signals cannot be accurately calculated from the data in that condition.

The equation (C) can be transformed as follows:

$$2(Lt-Lr)/L = \phi1/\phi2 \tag{D}$$

This equation (D) teaches that the ratio between the variations in phase difference of the base optical path and the measuring optical path equals the ratio between the optical path differences. That is, when the signal of the base optical path (the signal of the light receiver 155) and the signal of the measuring optical path (the signal of the light receiver 144) are compared with each other by varying the wavelength by a given amount, the ratio between the phase variations always equals the ratio between the optical path differences at the identical point of time because the variation of the phase difference is proportional to the optical path difference. This holds true, even if the wavelength emitted from the semiconductor laser 111 is variously varied, as long as the wavelength is consecutive. Therefore, the optical path difference of the base optical path is first arranged to be much longer than the measuring optical path, the interference signal of the measuring optical path is then sampled by means of the interference signal of the base optical path as a trigger signal, and the sampled data are arranged in order, so that the signals each having the same period in appearance can be obtained.

To explain the above more in detail, a single trigger signal is first generated for every period of the interference signal from the base optical path, and then the measuring signal is sampled by means of this trigger signal. Writing the sampled measuring signal in a memory 306 signifies that a trigger indefinite in period is replaced with a constantly spaced memory address for convenience. Since the ratio of the period of the measuring signal to the period of the trigger is constant, the signal in the memory is a signal constant in period. Like this, the signal is memorized in the memory 306 every each pulse.

Next, an analysis of the period is made from the memorized data. For this analysis, random noises are obviated on average with respect to a plurality of pulses (128 pulses, for example) because a practical signal has noises.

The period T obtained here signifies the ratio of the signal to the trigger, i.e., $\phi1/\phi2 = T$. According to the equation (D), Lt-Lr is immediately obtained from the period T. Signals of light reflected from different surfaces of the eyeball are selected when the analysis of the period is made.

Figure 2:
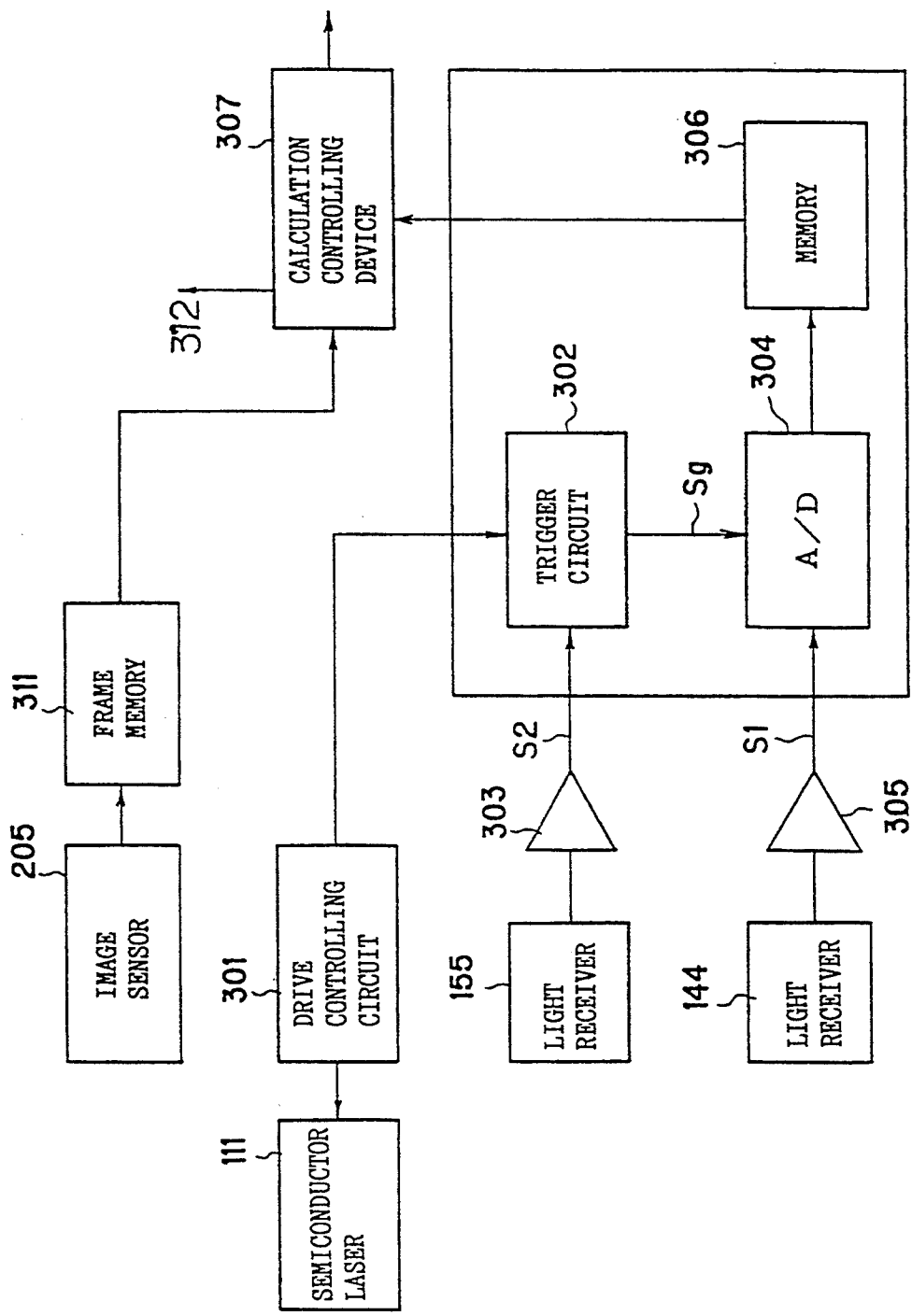
FIG. 2 is a block diagram showing a control system for calculating the length of an eye axis.

FIG. 2 is a block diagram showing a signal processing circuit for obtaining the optical path length Lt-Lr by the method described above.

The arrangement and action of the circuit are hereinafter described with reference to waveforms shown in FIG. 3.

In FIG. 2, the numeral 301 denotes a drive controlling circuit for supplying a pulse current (see (a) of FIG. 3) to the laser 111 to drive it, and controlling the temperature of the chip of the laser 111 by means of a Peltier effect type of element (not shown). The numeral 302 denotes a trigger circuit for outputting a trigger signal Sg shown in (e) of FIG. 3 every each period of the signal S2 output from the light receiver 155 via an amplifier 303. The A/D converter 304 converts the signal S1 output via an amplifier 305 from analogue to digital by using the trigger signal Sg as a timing signal. The numeral 306 denotes a memory for memorizing a digital value converted by the A/D converter 304. As shown in (f) of FIG. 3, the memory 306 memorizes the digital value corresponding to the amplitude of the signal S1. A calculation controlling device 307 performs a period analysis on the basis of the data memorized in the memory 306 to obtain the period T. According to the equation (D), the optical path length Lt-Lr is calculated from this period T.

On the other hand, the ring light illuminating optical system 201 of the cornea distance measuring optical system 200 illuminates the cornea Ea of the eye E with ring-shaped pattern light which is parallel in rays of light in meridional section. This pattern light is reflected from the cornea Ea and forms a ring-shaped virtual image I thereon. The reflected light is guided to the half mirror 202 through the objective lens 125 and the dichroic mirror 124 and divided into two rays of light. One of the two is once imaged as a ring-shaped aerial image Ia through the relay lens 211 and then imaged as a ring image i1 (see FIG. 4) on a light receiving surface 205a of the two-dimensional imaging element (image sensor) 205 via the mirror 212, the relay lens 213, the diaphragm 214, the half mirror 203 and the image forming lens 204. The imaging power of this ring image I1 is 0.5 times in this embodiment.

Figure 4:
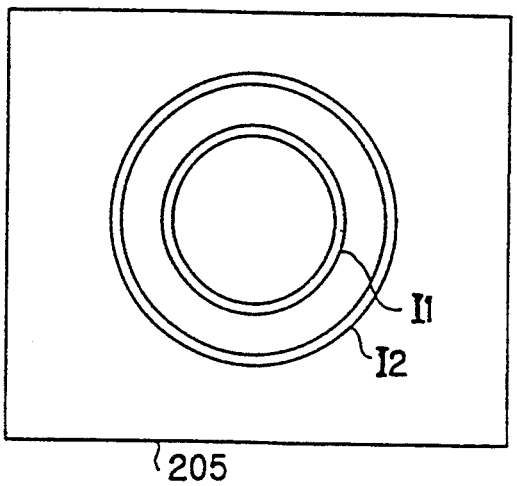
FIG. 4 is an illustration showing ring-shaped images formed on a light receiving surface of a two-dimensional imaging element.

The other one of the two reflected rays of light is reflected from the mirror 221 of the second imaging optical system 220, then once imaged as an aerial image 123 through the objective lens 125 and then forms a ring image I2 on the light receiving surface 205a of the two-dimensional imaging element (image sensor) 205 through the mirror 222, the relay lens 223, the mirror 224, the diaphragm 225, the half mirror 203, and the image forming lens 204, as shown in FIG. 4. The imaging power of this ring image I2 is set to be larger than that of the ring image I1.

The diaphragm 214 serves as a second diaphragm and is relayed to the neighborhood of the focusing position behind the objective lens 125 by the relay lenses 213, 211 and a conjugate image 214' is formed at the focusing position. The first imaging optical system 210 is generally telecentric toward the object side.

The diaphragm 225 serves as a first diaphragm and is relayed to the forward of the eye E (forward of the objective lens 125) by the relay lens 223. And a conjugate image 225' is formed in a position 25 mm to 50 mm away forward from the eye E here.

This embodiment will be described more in detail with reference to FIGS. 5 and 6 which schematically show the relationship between the objective lens 125 and the diaphragms 214, 225.

Figure 5:
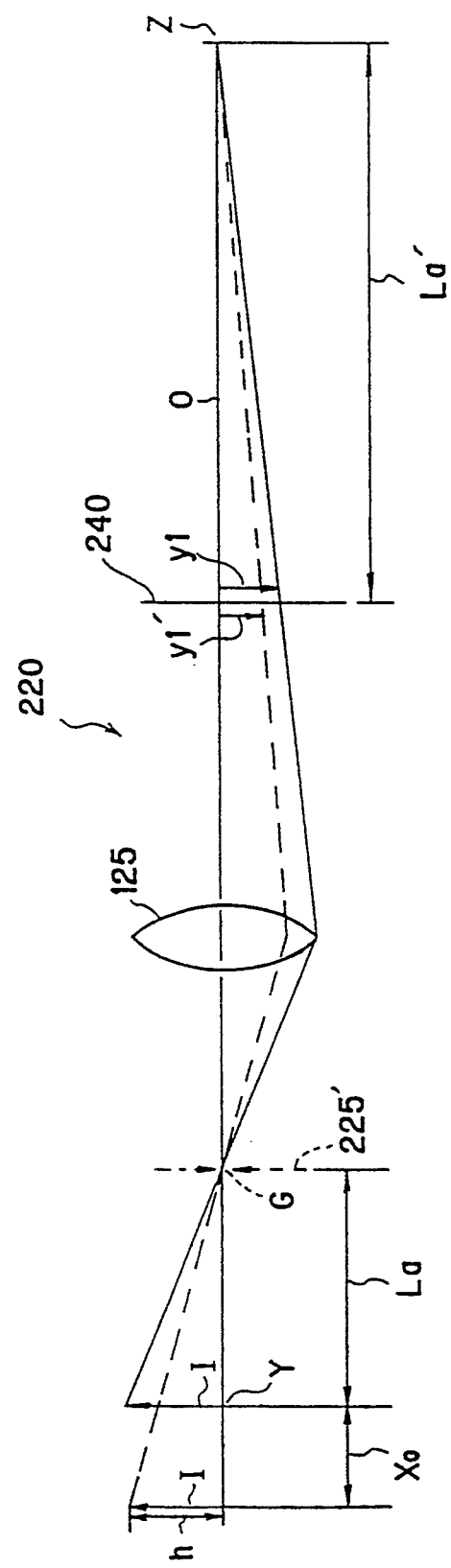
FIG. 5 is a schematic view showing a diaphragm and an objective lens of a second imaging optical system of a cornea distance measuring optical system.
Figure 6:
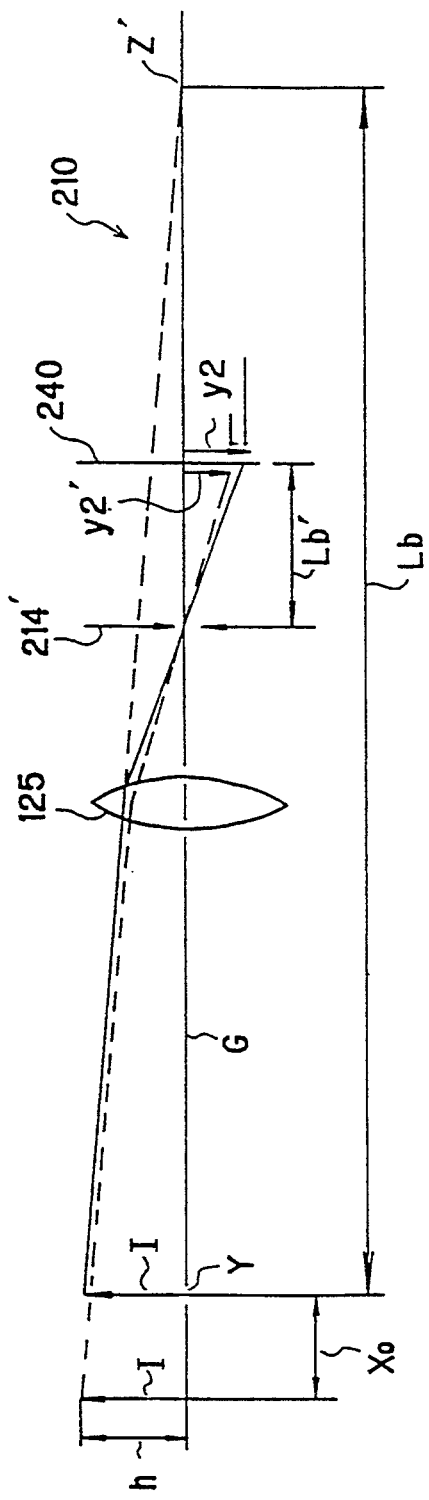
FIG. 6 is a schematic view showing a diaphragm and an objective lens of a first imaging optical system of the cornea distance measuring optical system.

FIGS. 5 and 6 illustrate an optical path of the second imaging optical system and an optical path of the first imaging optical system, respectively.

In this embodiment, an origin G is set to one point on an optical axis 0 where the conjugate image 225' of the diaphragm 225 is formed, and a base position Y is set to a position away in the direction of the optical axis 0 from the origin a by a distance L1. The location of this base position Y is deliberately determined so that the ring images I1 and I2 are not defocused. An object having a height h (this height is equal to the radius of the ring image I) is placed at this base position Y. The height of an image formed on the light receiving surface 205a (position where the two-dimensional imaging element 205 is located) by the second imaging optical system 220 at this time is represented by y1 and the height of another image formed on the light receiving surface 205a by the first imaging optical path 210 is represented by y2. Then, this known object is moved by a distance X0 and the heights of the images in these new positions are represented by y1' and y2', respectively.

Further, a distance from the light receiving surface 205a to a point Z is represented by La', a distance from the base position Y to a point Z' is represented by Lb, and a distance from the diaphragm 214' to the light receiving surface 205a is represented by Lb'. Further, a magnifying power of the objective lens 125 of the first imaging optical system 210 is represented by $\beta 1$ and a magnifying power of the objective lens 125 of the second imaging optical system 220 is represented by $\beta 2$.

Then, the following relations can be obtained.

$$h/La = (y1 \cdot \beta 1)/La' \tag{1}$$

$$h/(La + X0) = (y1' \cdot \beta 1)/La' \tag{2}$$

$$h/L2 = y2/(\beta 2 \cdot Lb') \tag{3}$$

$$h/(L2 + X0) = y2'/(\beta 2 \cdot Lb') \tag{4}$$

Presuming that the magnifying power $\beta 1$, and the distances L1, L1' are all constant in the above-mentioned equations (1) and (2), if the following replacement is made, $$K1 = (\beta 1 \cdot La)/La'$$

$$K2 = \beta 1/La'$$

then the equations (1) and (2) are rewritten as follows:

$$h = K1 \cdot y1 \tag{5}$$

$$h = K1 \cdot y1' + K2 \cdot y1' \cdot X0 \tag{6}$$

Likewise, presuming that the magnifying power $\beta 2$, and the distances Lb, Lb' are all constant in the above-mentioned equations (3) and (4), if the following replacement is made, $$K3 = Lb/(\beta 2 \cdot Lb')$$

$$K4 = 1/(\beta 2 \cdot Lb')$$

then the equations (3) and (4) are rewritten as follows:

$$h = K3 \cdot y2 \tag{7}$$

$$h = K3 \cdot y2' + K4 \cdot y2' \cdot X0 \tag{8}$$

Now, the constants K1, K2, K3, and K4 can be determined by actually measuring the height h of the object and the height y of the image.

That is, by rewriting the equations (5) and (6), the following equations can be obtained.

$$K1 = h/y1 \tag{9}$$

$$K2 = (h/y1) \cdot (y1 - y1)/(y1' \cdot X0) \tag{10}$$

$$K3 = h/y2 \tag{11}$$

$$K4 = (h/y2) \cdot (y2 - y2')/(y2' \cdot X0) \tag{12}$$

Thus, by actually measuring the height h of a known object as well as the height of its image, the constants K1, k2, K3 and k4 are obtained.

Next, there will be described how the measurement is carried out when the height h of an object and the distance X from the base position Y are unknown. In this case, a distance X is substituted for the distance X0 in the equations (2) and (4). Further, y1 and y2 are substituted for y1' and y2'.

Then, the following equations are obtained.

$$h = K1 \cdot y1 + K2 \cdot y1 \cdot X \tag{14}$$

$$h = K3 \cdot y2 + K4 \cdot y2 \cdot X \tag{15}$$

If the above simultaneous equations are simultaneously solved for the distance X and the height of the object, the following answers can be obtained.

$$X = (K3 \cdot y2 - K1 \cdot y1)/(K2 \cdot y1 - K4 \cdot y2) \tag{16}$$

$$h = K1 \cdot y1 + K2 \cdot y1 \cdot X = (K2 \cdot K3 - K1 \cdot K4)y1 \cdot y2/(K2 \cdot y1 - K4 \cdot y2) \tag{17}$$

Therefore, by measuring the image heights y1 and y2, the distance from the base position Y to the object can be measured.

Next, the measurements of the radius R of curvature of a cornea and the position of its vertex will be described with reference to FIG. 7.

Figure 7:
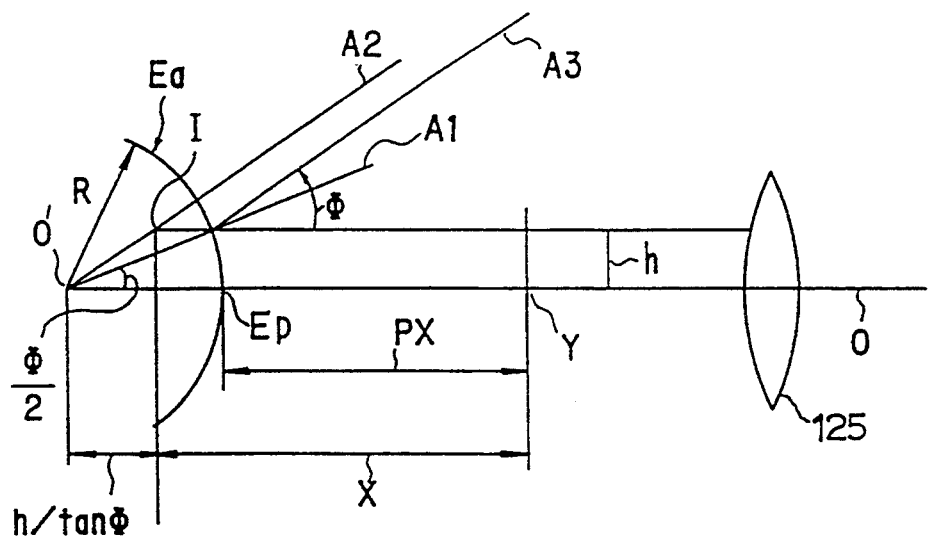
FIG. 7 is an illustration showing the measurement of a corneal radius of curvature and its vertex position.

In FIG. 7, the radius (the long diameter or short diameter when it resembles an ellipse) of a ring image I is presumed to be the height h of the object. At this time, the object height h is determined by a meridional ray. If the diameter of the ring image is approximately 3 mm, the angle $\phi$ becomes approximately 20°, and the under-listed paraxial calculating equation cannot be used.

$$h = (r \cdot \sin \phi)/2$$

Therefore, if the distance Lb is set to be large enough, the angle $\phi$ is normally held to be constant and one measured by the second imaging optical system 220 passing the diaphragm 225 is used as the object height h, an equation based on the under-listed reflexive law can be used.

$$h = r \cdot \sin(\phi/2)$$

If the above equation rewritten, the following equation is obtained.

$$r = h/\sin(\phi/2) \tag{18}$$

Presuming that the distance La is set such that an angle between light beams passing the diaphragms 214 and 225 does not become large excessively, if the object height h obtained by the equation (17) is substituted into the above-mentioned equation (18) and if the position of the corneal vertex EP is presumed to be a distance Px from the base position Y, the following equation can be obtained.

$$Px = X - (r - h/\tan \phi) \tag{19}$$

The equation (19) for the position of the corneal vertex is presumed to require the presence of the ring image on the optical path of the spherical surface. And it is subject to an influence of spherical aberration. However, the influence is supposedly not decisive and accordingly it can be amended based on experimental data.

Accordingly, the distance Px is obtained from the diameters of the ring images I1 and I2 formed on the two-dimensional imaging element 205.

To obtain the distance Px, a frame memory 311 (see FIG. 2) memorizes the data of the ring images I1 and I2 and then the calculation controlling device 307 calculates on the basis of the data.

In FIG. 7, 0' represents the center of curvature of the cornea, A1 and A2 each represent a normal line of a spherical surface when the cornea Ea is regarded as a spherical surface, and A3 represents an incident ray on the cornea.

Figure 8:
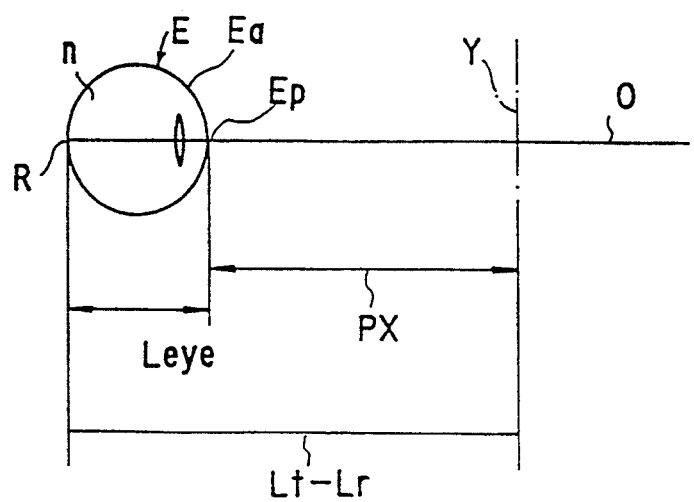
FIG. 8 is an illustration showing the relationship between an eye fundus distance, a corneal vertex distance, and an eye axis length.

FIG. 8 shows the relationship between an eye fundus distance, a corneal vertex distance, and an eye axis length each obtained in such a way as above. In this case, the base position Y and the position of the reference mirror coincides with each other.

A reduced value Leye of the eye axis length to the refractive index of air can be obtained by subtracting the distance Px from the optical path length Lt-Lr obtained by the interference method. If the base position Y and the position of the reference mirror 133 do not coincide with each other, a difference between the position Y and that of the mirror 133 is predetermined and it can be amended when calculated. Accordingly, the eye axis length can be obtained by dividing the value Leye by an average refractive index of the eyeball. These calculations are also carried out by the calculation controlling device 307. Further, the calculation controlling device 307 causes a display (not shown) to display the results and a printer (not shown) to print them.

By the way, the eye fundus distance measuring optical system 100 is arranged such that circularly polarized light is projected onto the retina Er through the Babinet compensator and the reflected light therefrom is received as linearly polarized light perpendicular to the direction of the polarization of the polarizer 114.

Circularly polarized light is produced when X and Y components of linearly polarized light, which are each polarized perpendicularly to an axis (referred to as Z-axis) of a direction into which light proceeds, are different in phase difference from each other by a quarter wavelength (90°). But the amplitudes of the X and Y components are assumed to be the same. The Babinet compensator 128 can transform a beam of linearly polarized light into X and Y components of light perpendicular to each other owing to birefringence of its crystal, and vary the phase difference of the light of the X and Y components within the range of $\lambda/4 \pm \alpha$ consecutively.

If a $\alpha=0$, linearly polarized light can be transformed into circularly polarized light. This circularly polarized light is projected to a reflecting surface and then is caused to pass through the same Babinet compensator 128, so that linearly polarized light perpendicular to the former direction of polarization is obtained.

Since a real eyeball has, for example, birefringence, the reflected light from the eye fundus becomes elliptically polarized light even if circularly polarized light is projected thereonto. Therefore, the reflected light transmitted again through the Babinet compensator 128 becomes not perfectly circularly polarized light but elliptically polarized light. Further, since the elliptically polarized light is received through the analyzer 142, the intensity of the received light is lower than that of linearly polarized light.

The Babinet compensator 128 is used for compensating birefringence of the eyeball and so forth.

Figure 9:
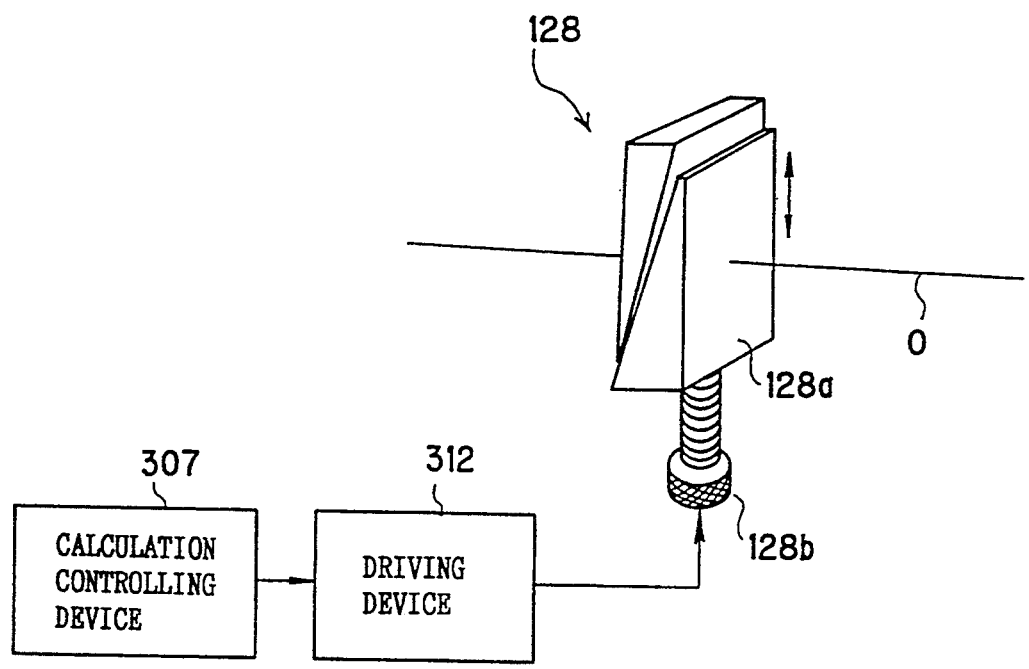
FIG. 9 is a perspective view showing an arrangement of a Babinet compensator.

As shown in FIG. 9, the Babinet compensator 128 includes a wedge plate 128a and a micrometer 128b.

The wedge plate 128a is moved up or down by the micrometer 128b. In response to the motion of the wedge plate 128a, the phase difference $(\lambda/4 \pm \alpha)$ is consecutively varied as described above.

Presuming that the phase difference between two polarization components of light perpendicular to each other is $(\lambda/4)+\alpha$ when they are transmitted through the Babinet compensator 128, if the phase difference between these components is displaced by $\beta$ owing to, for example, the birefringence of the eyeball, the phase difference between the components perpendicular to each other of light reflected from the eye fundus becomes $(\lambda/4)+(\alpha+\beta)$. When this reflected light from the eye fundus is transmitted through the Babinet compensator 128, the phase difference between the components is again displaced by $(\lambda/4)+\alpha$.

In order that the reflected light from the eye fundus become linearly polarized light perpendicular to the former linearly polarized light when transmitted through the Babinet compensator 128, a phase difference between the measuring light which has not yet entered the Babinet compensator 128 and the reflected light from the eye fundus which has already passed through the Babinet compensator 128 must be displaced by $\lambda/4$.

Accordingly, the following equation is satisfied.

$$(\lambda/4)+(\alpha+\beta)+(\lambda/4)+\alpha=\lambda/2$$

This is transformed as follows:

$$2\alpha=-\beta$$

Therefore, a position of the wedge plate 128a is adjusted so as to cause the phase difference between the components of the polarized light perpendicular to each other to become $(\lambda/4)-(\beta/2)$ by means of the Babinet compensator 128. As a result, the reflected light which has passed through the Babinet compensator 128 becomes linear polarized light perpendicular to the polarization direction of the measuring light. The wedge plate 128a is moved such that the amount of light received by the light receiver 144 is maximum. A driving device 312 serves to rotate the micrometer 128b.

To determine a position of the wedge plate 128a where the amount of light received by the light receiver 144 is maximum, the wedge plate 128a is automatically moved from the lowest position to the highest position thereof, for example. When moved, a position of the wedge plate 128a is found where the amplitude memorized in the memory 306 is maximum. The wedge plate 128a is moved to that position and is fixed there, and then the eye axis length is automatically measured.

As described above, the Babinet compensator 128 can transform the reflected light from the eye fundus reaching the analyzer 142 into linearly polarized light perpendicular to the polarization direction of the measuring light passing through the polarizer 114, and accordingly the amount of light passing through the analyzer 142 can be increased. In other words, interference signals of the light receiver 144 can be leveled up. Further, since the reflected light from the eye fundus is transformed into linearly polarized light and then is caused to enter the light receiving element 144 by means of a polarization beam splitter 121, disadvantageous reflected light produced by, for example, the objective lens 125 is prevented from entering the light receiving element 144.

The invention is not limited to the above embodiment and is applicable to the following variant forms.

(1) The measuring means is not limited to such as to make interference between the reflected light from the eye fundus and the reflected light from the reference mirror 133 and measure its optical path difference (distance between the reference surface of the mirror 133 and the eye fundus) in the above embodiment.

For example, a position of the reference mirror 133 is arranged to be movable in the direction of the optical axis by using a measuring beam of light having a short coherent length. The position of the reference mirror 133 is determined from an interference signal obtained when an optical path length between the beam splitter 121 and the eye fundus equals an optical path length between the beam splitter 121 and the reference mirror 133. And a distance between the reference mirror 133 and the eye fundus is measured.

(2) The invention is also applicable to a measuring instrument in which interference is made between the reflected light from the cornea and the reflected light from the eye fundus, not between the reflected light from the eye fundus and the reflected light from the reference mirror 133. But, care must be taken to that the reflected light from the cornea has no birefringence.

(3) The invention is also applicable to such a measuring instrument as not to make use of interference.

For example, by modulating the intensity of a beam of light emitted from the light source, a propagation time of the measuring beam of light is calculated from the phase of a modulation signal included in a light receiving signal to measure an intraocular length of the eye.

(4) If the light source emits a beam of linearly polarized light, the polarizer 114 does not have to be disposed in the optical system.

(5) In the above embodiment, to obviate reflection noises of the optical system, the polarization direction of the measuring beam of light emitted from the light source is caused to become perpendicular to the polarization direction of the reflected light received by the light receiver 144. However, the two directions do not have to be perpendicular to each other if the reflection noises of the optical system are made small enough.

Even in this case, a phase difference between the components of the reflected light polarized in the direction perpendicular to each other is produced owing to the birefringence of the eyeball when the eye axis length is calculated from an interference signal obtained by making interference between the reflected light from the eye fundus and the reflected light from the reference surface. Therefore, if interference is made between the two reflected light beams, the contrast of the interference signal may decrease because they include different components in phase. An amendment to the birefringence is equally effective for this case. This amendment is such as to cause the polarization direction of the reflected light which has passed through the compensator to coincide with the polarization direction of the reference light, not to cause the polarization direction of the reflected light to become perpendicular to the linearly polarized light emitted from the light source.

In other words, the above embodiment intends that the sum total of the phase difference due to the birefringence of the eyeball and the phase difference due to the Babinet compensator 128 is $\lambda/4$ (for one way). However, the birefringence of the eyeball may be canceled or an optional phase difference may be adjusted so as to coincide with the polarization direction of the reference light. This variant form shows an amendment to the birefringence of the eyeball in a case where each polarized light of the illuminating light and the received light does not have to be made perpendicular to the other. Therefore, the $\lambda/4$ plate 132 disposed in front of the reference surface is not an indispensable condition. Further, the Babinet compensator 128 may be disposed not only immediately in front of the eye but also in an optical path where both the illuminating light incident on the eye fundus and the reflected light from the eye fundus travel.

What is claimed is:

1. An intraocular length measuring instrument, comprising: a polarization component substantially perpendicular to said measuring beam of linearly polarized light emitted from the light source portion, said phase compensating means being disposed between the eye to be measured and said beam splitter.

2. An intraocular length measuring instrument, comprising:
   a light source portion for emitting a measuring beam of light;
   a measuring optical system for projecting said measuring beam onto an intraocular object to be measured;
   a beam splitter for separating a part of said measuring beam from said measuring beam;
   a reference optical system for guiding said separated part of light to a reference mirror;
   an interference optical system for making interference between measuring beam of light reflected from the eye fundus and a beam of light reflected from said reference mirror;
   a light receiving portion for receiving said interference light made by said interference optical system; and
   phase compensating means for setting a compensation value in consideration of birefringence of the intraocular object in order to cause a beam of light reflected from said intraocular object to have a given phase difference with respect to said measuring beam of light projected onto said intraocular object, said phase compensating means being disposed between the eye to be measured and said beam splitter.

3. An intraocular length measuring instrument according to claim 1 or 2, wherein said phase compensating means is a Babinet compensator.

* * * * *

UNITED STATES PATENT AND TRADEMARK OFFICE
CERTIFICATE OF CORRECTION

PATENT NO. : 5,349,399
DATED : September 20, 1994
INVENTOR(S) : Akihiko SEKINE

It is certified that error appears in the above-indentified patent and that said Letters Patent is hereby corrected as shown below:

Claim 1, column 14, line 25, after ":" insert the following:

-- a light source portion for emitting a measuring beam of linearly polarized light;

a beam splitter for separating a beam of light reflected by an intraocular object to be measured from said measuring beam of light projected from said light source portion onto the intraocular object;

a light receiving portion for receiving said reflected beam of light separated by said beam splitter; and

UNITED STATES PATENT AND TRADEMARK OFFICE
CERTIFICATE OF CORRECTION

PATENT NO. : 5,349,399
DATED : September 20, 1994
INVENTOR(S) : Akihiko Sekine

It is certified that error appears in the above-indentified patent and that said Letters Patent is hereby corrected as shown below:

phase compensating means for [transforming] <u>setting a compensation value in consideration of birefringence of the intraocular object in order to transform</u> said beam of light reflected from the intraocular object into a beam of light having--

Signed and Sealed this

Twenty-fifth Day of April, 1995

Attest:

BRUCE LEHMAN

*Attesting Officer*   *Commissioner of Patents and Trademarks*